United States Patent
Shibata et al.

(10) Patent No.: US 10,416,048 B2
(45) Date of Patent: Sep. 17, 2019

(54) COLLECTING APPARATUS

(71) Applicants: Sibata Scientific Technology Ltd., Soka-shi (JP); Veritas System Ltd., Tokyo (JP)

(72) Inventors: Masatoshi Shibata, Soka (JP); Yoshihiro Suzuki, Soka (JP)

(73) Assignees: Sibata Scientific Technology Ltd., Soka-shi (JP); Veritas System Ltd., Tokyo (JP)

( * ) Notice: Subject to any disclaimer, the term of this patent is extended or adjusted under 35 U.S.C. 154(b) by 65 days.

(21) Appl. No.: 15/311,710

(22) PCT Filed: Jul. 14, 2014

(86) PCT No.: PCT/JP2014/068735
§ 371 (c)(1),
(2) Date: Nov. 16, 2016

(87) PCT Pub. No.: WO2016/009486
PCT Pub. Date: Jan. 21, 2016

(65) Prior Publication Data
US 2017/0082525 A1    Mar. 23, 2017

(51) Int. Cl.
  *G01N 1/22*  (2006.01)
  *G01N 1/24*  (2006.01)
(52) U.S. Cl.
  CPC .......... *G01N 1/2273* (2013.01); *G01N 1/2214* (2013.01); *G01N 2001/2276* (2013.01); *G01N 2001/245* (2013.01)
(58) Field of Classification Search
  CPC ................. G01N 2001/2276; G01N 2001/245
  See application file for complete search history.

(56) References Cited

U.S. PATENT DOCUMENTS

2004/0045376 A1*   3/2004   Van Netten .......... G01N 1/2205
                                                              73/863.23

FOREIGN PATENT DOCUMENTS

| GB | 2401174 A | 11/2004 |
| JP | 9196830 A | 7/1997 |
| JP | 2002153259 A | 5/2002 |

(Continued)

OTHER PUBLICATIONS

Machine English Translation of JP2012-026954—No date.*
Yuhi Watanabe et al., "Kyosei Sofushiki Passive Sampler (Semi-active Sampler)", pp. 27-29, English-language Abstract.

*Primary Examiner* — Jill A Warden
*Assistant Examiner* — Dwayne K Handy
(74) *Attorney, Agent, or Firm* — The Webb Law Firm

(57) ABSTRACT

A collecting apparatus comprises: a housing which is long and includes a housing space capable of housing a collecting member, the housing having formed therein an inflow port and an outflow port; a gas flow generator that generates a gas flow within the housing space; and a holding portion that holds the collecting member in a position that the gas flow flows, the inflow port being formed on a more upstream side than the collecting member held by the holding portion, and the outflow port being formed on a more downstream side than the collecting member held by the holding portion, and the outflow port opening toward the downstream side such that air that has flowed out from the outflow port flows along a housing outer surface on a more downstream side than the outflow port.

4 Claims, 6 Drawing Sheets

(56) References Cited

FOREIGN PATENT DOCUMENTS

| JP | 2003114176 A | 4/2003 |
| JP | 2004301749 A | 10/2004 |
| JP | 200911265 A | 1/2009 |
| JP | 2010124711 A | 6/2010 |
| JP | 2012-26954 A | 2/2012 |
| JP | 2013156067 A | 8/2013 |

\* cited by examiner

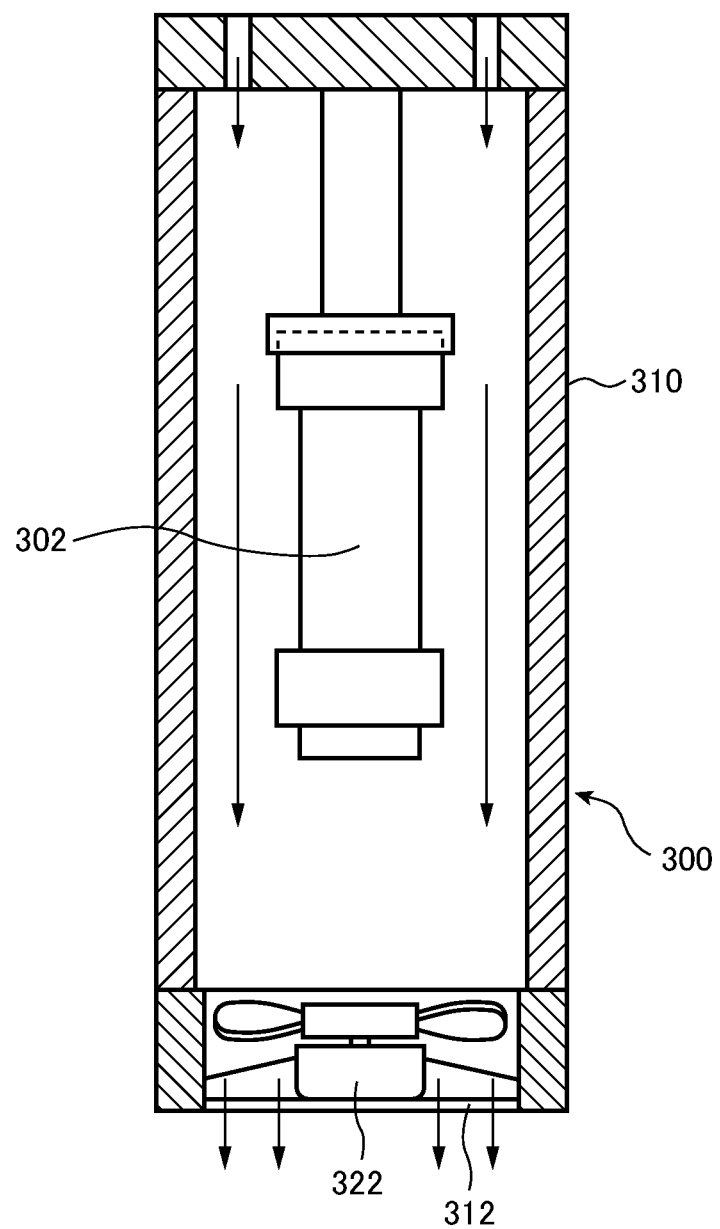

COLLECTING APPARATUS

CROSS-REFERENCE TO RELATED APPLICATION

This application is the United States national phase of International Application No. PCT/JP2014/068735 filed Jul. 14, 2014, the disclosure of which is hereby incorporated in its entirety by reference.

TECHNICAL FIELD

The present invention relates to a collecting apparatus that collects in a collecting material a substance-to-be-collected such as a volatile organic compound (VOC) or a semi-volatile organic compound (SVOC) floating in the atmosphere.

BACKGROUND ART

Conventionally, a passive sampler that is exposed to the atmosphere and performs collection by natural diffusion, has been employed in collection of a substance-to-be-collected such as formaldehyde floating in the atmosphere (Patent Document 1). This passive sampler sets a substance-to-be-collected concentration always to zero at a collecting inner surface and maintains a constant concentration gradient with an inlet port that is a collecting outer surface contacting a collecting atmosphere whose concentration is higher than that at the collecting inner surface, by means of an absorbing agent or collecting agent provided within the passive sampler, thereby utilizing a movement diffusion phenomenon of substance concentration to collect the substance-to-be-collected.

A collecting rate per unit area of the passive sampler, that is, a unit collecting speed J is determined by a concentration gradient (C/L) and a molecular diffusion coefficient D [cm$^2$/sec] of a diffusing substance, and this can be expressed by the so-called Fick's first law of diffusion equation (J=D× C/L). Now, in Fick's first law of diffusion equation, C expresses a concentration [μg/ml] in a periphery, and L expresses a diffusion length [cm], that is, a length from the inlet port of the passive sampler to a collecting surface. Moreover, as shown in equation (SR=A×D×C/L), a total collecting speed SR of the passive sampler can be obtained by multiplying the collecting speed per unit area J (J=D× C/L) by a collecting area A. Generally, this is called a sampling rate SR, and is known as a characteristic collecting speed with respect to a certain specific substance-to-be-collected of the passive sampler. This sampling rate SR is expressed by a dimensional unit such as [μg/(ppm×min)], and this is known to make it possible to find a concentration C' of the substance-to-be-collected in the atmosphere, from a value of the sampling rate SR and a value of a collection amount M [μg] and collection time t [min] obtained from a post-collection analysis result, based on equation (C'=M/(SR×t)).

However, there is a problem that because collection is performed by natural diffusion, the sampling rate SR of the passive sampler does not indicate a constant value due to an influence of wind speed on-site, and the sampling rate SR fluctuates significantly particularly in the case of a low wind speed. This is conceivably because a peripheral wind speed of the passive sampler decreasing causes a diffusion concentration gradient to extend from the passive sampler whereby a concentration gradient gets created outside the passive sampler and a value of the diffusion length L greatly changes. As shown in FIG. 8, such "extension of diffusion field" is prominent at a wind speed of under 0.5 m/sec, particularly at a low wind speed of 0.1 m/sec or less. Now, FIG. 8 is a graph showing results of verification carried out by the applicant of the present application using the passive sampler that shows a relationship between collection amount of the passive sampler and wind speed under a steady environment, and, in order to clarify a reference, the vertical axis in FIG. 8, that is, the collection amount of the passive sampler is expressed by a ratio [%] to a collection amount obtained by an active method where collection is performed using a pump (collection amount of passive sampler/collection amount by active method).

In order to prevent such "extension of diffusion field", it is conceivable to, for example, increase a film thickness or reduce an opening diameter or opening ratio of the passive sampler to secure a larger diffusion length L and thereby apparently reduce the extension. However, it is impossible in principle to set the extension to 0, and in an actual measurement environment, the wind speed is constantly fluctuating and the diffusion length L also ends up fluctuating based on the wind speed fluctuation, hence it is close to impossible to predict and make constant an apparent diffusion length L in the passive sampler. As a result, there is a problem that in the case of accurately measuring concentration of a substance-to-be-collected in the atmosphere using the passive sampler, it is necessary to employ a general calculation method that finds the sampling rate SR as an actual value according to a measurement site or compares with an active method using the likes of a pump to find the sampling rate SR beforehand as a representative value, and employ this sampling rate SR, and the method is complex and moreover an inferior method whose accuracy is lower than that of the active method.

As a collecting apparatus capable of solving such problems, the applicant of the present application proposes, for example, a collecting apparatus 300 shown in FIG. 9 (Patent Document 2). As shown in FIG. 9, this collecting apparatus 300 is configured capable of housing a passive sampler 302 within a housing 310, and is configured such that a wind speed can be forcibly generated within the housing 310 by a flow means such as a fan 322. Such a collecting apparatus 300 enables an influence of wind speed on-site to be eliminated, hence makes it possible to achieve stable collection of the substance-to-be-collected.

PRIOR ART DOCUMENT

Patent Document

[Patent Document 1] JP 2003-114176 A
[Patent Document 2] JP 2012-26954 A

SUMMARY OF INVENTION

Problem to be Solved by the Invention

However, as shown in FIG. 9, the conventional collecting apparatus 300 has an outflow port 312 formed at one end in its longitudinal direction, hence there is a risk that when, for example, the device is housed in a confined space such as a breast pocket of an operator, the outflow port 312 gets blocked and stable collection of the substance-to-be-collected cannot be performed. Therefore, in the conventional collecting apparatus 300, there is a problem that it is difficult to execute a method of collecting where, for example, collection of the substance-to-be-collected is performed while the device is being carried housed in the likes of a breast pocket of an operator.

Accordingly, the present invention has an object of providing a collecting apparatus that can perform collection of the substance-to-be-collected without any problem, even when, for example, collection of the substance-to-be-collected is performed while the device is being carried housed in the likes of a breast pocket of an operator.

Means for Solving the Problem

In order to achieve the above-described object, a collecting apparatus according to the present invention is a collecting apparatus that employs a collecting member to collect a substance-to-be-collected in the atmosphere, and comprises: a housing which is long and includes a housing space capable of housing the collecting member, the housing having formed therein an inflow port and an outflow port, the inflow port enabling air in the atmosphere to flow in to said housing space, and the outflow port enabling air in the housing space to flow out; a gas flow generator that generates a gas flow within the housing space, so as to allow air in the housing space to flow in from the inflow port and cause that air to flow toward the outflow port; and a holding portion that holds the collecting member in a position that the gas flow flows, the inflow port being formed on a more upstream side than the collecting member held by the holding portion, and the outflow port being formed on a more downstream side than the collecting member held by the holding portion, and the outflow port opening toward the downstream side such that air that has flowed out from said outflow port flows along a housing outer surface on a more downstream side than said outflow port.

In the collecting apparatus according to the present invention, it is preferable that the housing comprises: an upstream side housing that includes the housing space; a downstream side housing connected to a downstream side of the upstream side housing; and a connecting portion that connects the upstream side housing and the downstream side housing, the connecting portion includes an outflow direction regulating wall portion of cylindrical shape provided projecting toward the downstream side housing so as to surround an outer surface of an upper end and close to the upper end of the downstream side housing, and a gap formed between an inner surface of the outflow direction regulating wall portion and the outer surface of the upper end and close to the upper end of the downstream side housing is configured to function as the outflow port.

In this case, it is preferable that the gas flow generator comprises: a fan that generates the gas flow; a control unit that controls drive of the fan; and a power supply unit that supplies electric power for driving the fan, and the control unit and the power supply unit are housed in the downstream side housing.

Moreover, in the collecting apparatus according to the present invention, it is preferable that the housing is formed in a cylindrical shape having its end side on an upstream side blocked, and a plurality of the inflow ports are formed at certain intervals in a circumferential direction of the housing, in a region of not more than three quarters of an entire region in the circumferential direction of the housing.

The collecting apparatus according to the present invention preferably further comprises: a turbulence generator provided on a more upstream side than the collecting member held by the holding portion, the turbulence generator being configured to render the gas flow in a turbulent state.

Advantages of the Invention

The collecting apparatus according to the present invention has its outflow port opening toward the downstream side such that air that has flowed out from the outflow port flows along the housing outer surface on a more downstream side than the outflow port, whereby even when the device is housed in a confined space, the outflow port is never blocked. Therefore, the present invention makes it possible to provide a collecting apparatus that can perform collection of the substance-to-be-collected without any problem, even when, for example, collection of the substance-to-be-collected is performed while the device is carried housed in the likes of a breast pocket of an operator.

BRIEF DESCRIPTION OF DRAWINGS

FIG. 9 is a cross-sectional view showing a schematic configuration of a conventional collecting apparatus.

EMBODIMENTS FOR CARRYING OUT THE INVENTION

Figure 1:
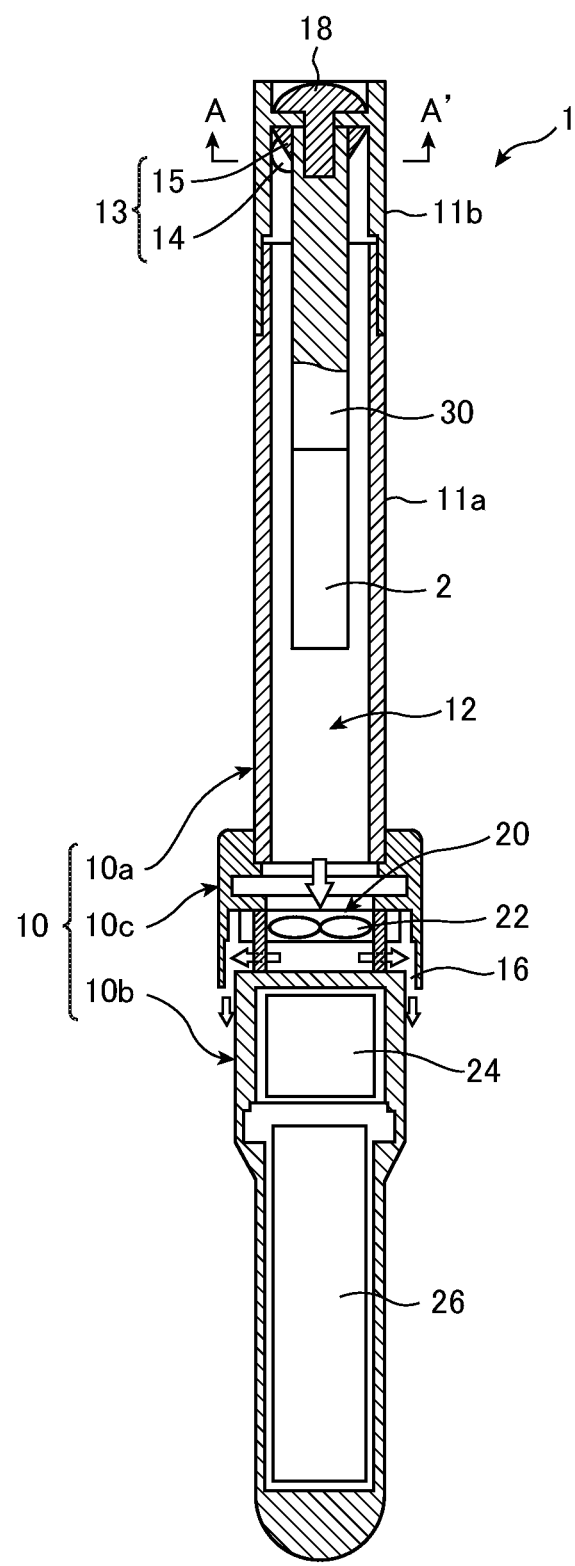
FIG. 1 is a cross-sectional view showing a schematic configuration of a collecting apparatus according to a first embodiment of the present invention.

Next, a collecting apparatus according to a first embodiment of the present invention will be described based on FIGS. 1 to 4. As shown in FIG. 1, a collecting apparatus 1 according to the first embodiment comprises: a housing 10 which is long and includes a housing space 12 capable of housing a collecting member 2, the housing 10 having formed therein an inflow port 14 and an outflow port 16, the inflow port 14 enabling air in the atmosphere to flow in to the housing space 12, and the outflow port enabling air in the housing space 12 to flow out; a gas flow generator 20 that generates a gas flow within the housing space 12, so as to allow air in the housing space 12 to flow in from the inflow port 14 and cause that air to flow toward the outflow port 16; a holding portion 30 that holds the collecting member 2 in a position that the gas flow flows; and a turbulence generator 13 that renders the gas flow in a turbulent state on a more upstream side than the collecting member 2.

As shown in FIG. 1, the housing 10 comprises: an upstream side housing 10a that includes the housing space 12; a downstream side housing 10b connected to a downstream side of the upstream side housing 10a; and a connecting portion 10c that connects the upstream side housing 10a and the downstream side housing 10b, and the housing 10 is configured so as to form a stick-type housing by these upstream side housing 10a, connecting portion 10c, and downstream side housing 10b being coaxially connected. The housing 10 is a compact housing having about the same size as a pen, that is, having a length in its longitudinal direction of about 10 or so cm, and having a diameter of about several cm, and is configured capable of being carried housed in the likes of a breast pocket of an operator such that the inflow port 14 is exposed, for example. Note that in the description below, an upstream side refers to an upstream side of a flow direction of a gas flow generated in the housing space 12, that is, an upper end side in the longitudinal direction of the housing 10, and a downstream side refers to a downstream side of a flow direction of a gas flow generated in the housing space 12, that is, a lower end side in the longitudinal direction of the housing 10.

As shown in FIG. 1, the upstream side housing 10a comprises: a housing main body 11a formed in a cylindrical shape; and a lid member 11b formed in a cylindrical shape having its upper end side blocked, the lid member 11b being configured freely attachable/detachable to/from an upper end side of the housing main body 11a. The housing space 12 capable of housing the collecting member 2 is defined by inner surfaces of these housing main body 11a and lid member 11b. The upstream side housing 10a preferably adopts a configuration having light blocking properties to provide a light blocking effect of sunlight, and so on, but is not limited to this.

The housing main body 11a is formed in a cylindrical shape having its upper end and lower end open, and has a diameter and length in an axial direction enabling a sufficient gas flow to be generated in a state where the collecting member 2 is housed therein. The upper end and close to the upper end of the housing main body 11a are formed with a thin wall so as to have an external diameter smaller than in another portion of the housing main body 11a. A screw (not illustrated) for attaching the lid member 11b is formed on an outer surface of this thin-walled portion of the housing main body 11a. A screw (not illustrated) for attaching the connecting portion 10c is formed on an outer surface of the lower end and close to the lower end of the housing main body 11a.

The lid member 11b is formed in a cylindrical shape having its upper end blocked and its lower end open and has largely the same diameter as the housing main body 11a. The lower end and close to the lower end of the lid member 11b are formed with a thin wall so as to have an internal diameter larger than in another portion of the lid member 11b, such that the thin-walled portion of the upper end and close to the upper end of the housing main body 11a are insertable therein. A screw (not illustrated) capable of engaging with the screw (not illustrated) formed in the upper end and the thin-walled portion of the upper end of the housing main body 11a is formed on an inner surface of this thin-walled portion of the lid member 11b.

Figure 2:
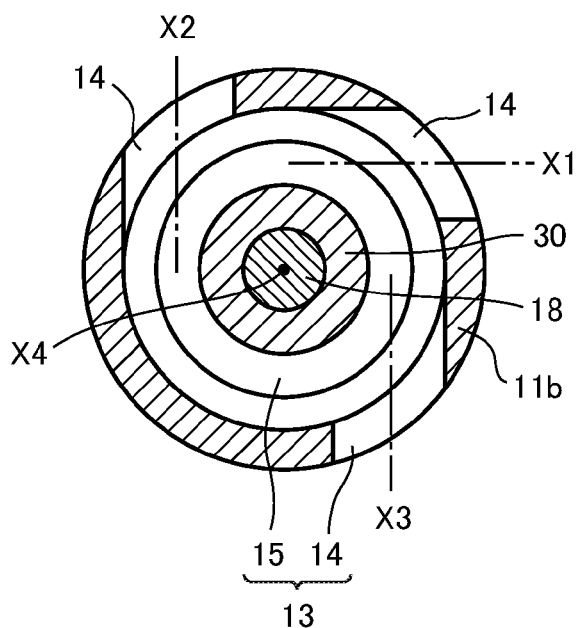
FIG. 2 is a cross-sectional view taken along the line A-A' of FIG. 1.

As shown in FIG. 2, formed in the lid member 11b is the inflow port 14 for allowing air in the atmosphere to flow in to the housing space 12 of the upstream side housing 10a. The inflow port 14 is a hole penetrating in a direction intersecting an axial direction of the lid member 11b, from an outer circumferential surface to an inner circumferential surface of the lid member 11b, and a plurality (in the first embodiment, three) of the inflow ports 14 are formed at certain intervals in a circumferential direction, in a region of not more than three quarters of an entire region in the circumferential direction of the lid member 11b. As shown in FIG. 2, these inflow ports 14 are formed having their positions misaligned in the circumferential direction such that each of respective central axes X1, X2, and X3 of these inflow ports 14 are not orthogonal to a central axis X4 of the lid member 11b, in a cross-section orthogonal to the axis of the lid member 11b. Each of the inflow ports 14 has a diameter enabling air in the atmosphere to flow into the housing space 12, and is configured so as not to hinder operation and function of the gas flow generator 20.

Figure 3:
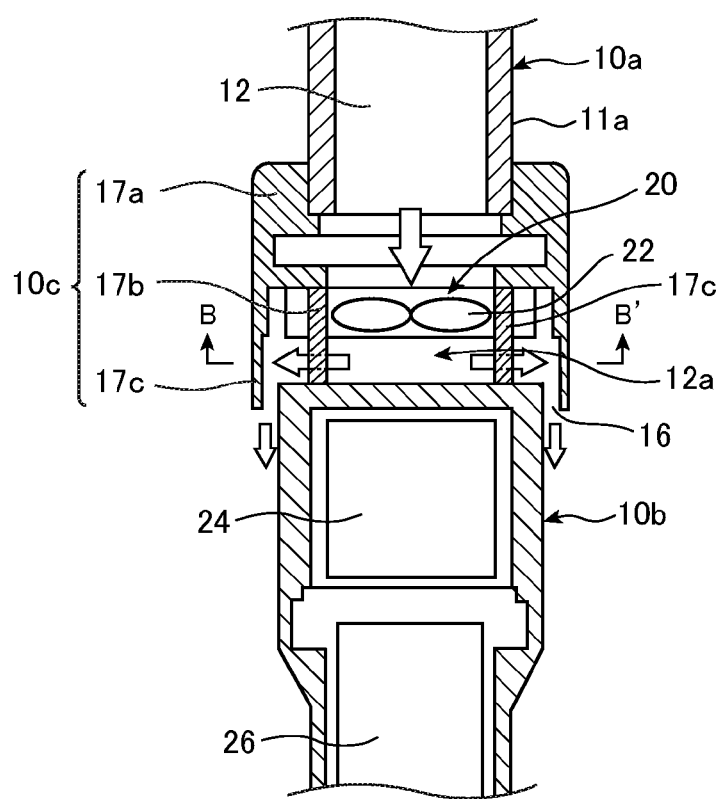
FIG. 3 is a cross-sectional view showing enlarged a schematic configuration of close to an outflow port of the collecting apparatus according to the first embodiment.

As shown in FIG. 3, the connecting portion 10c comprises: a connecting main body portion 17a configured capable of being connected to the housing main body 11a of the upstream side housing 10a; a plurality of connecting columns 17b configured capable of being connected to the downstream side housing 10b; and an outflow direction regulating wall portion 17c configured capable of regulating an outflow direction of air flowing out.

The connecting main body portion 17a is formed in a cylindrical shape having its upper end and lower end open, has largely the same internal diameter as an internal diameter of the housing main body 11a, and has a larger external diameter than external diameters of the housing main body 11a and downstream side housing 10b. That is, the connecting main body portion 17a has a shape expanded more outwardly in a circumferential direction than the housing main body 11a and downstream side housing 10b, such that an outer surface of the connecting main body portion 17a is positioned more outwardly in a circumferential direction than outer surfaces of the housing main body 11a and downstream side housing 10b. A screw (not illustrated) capable of engaging with the screw (not illustrated) formed in the lower end and close to the lower end of the housing main body 11a is formed on an inner surface of the upper end and close to the upper end of the connecting main body portion 17a, and the connecting main body portion 17a is configured freely attachable/detachable with respect to the housing main body 11a.

Figure 4:
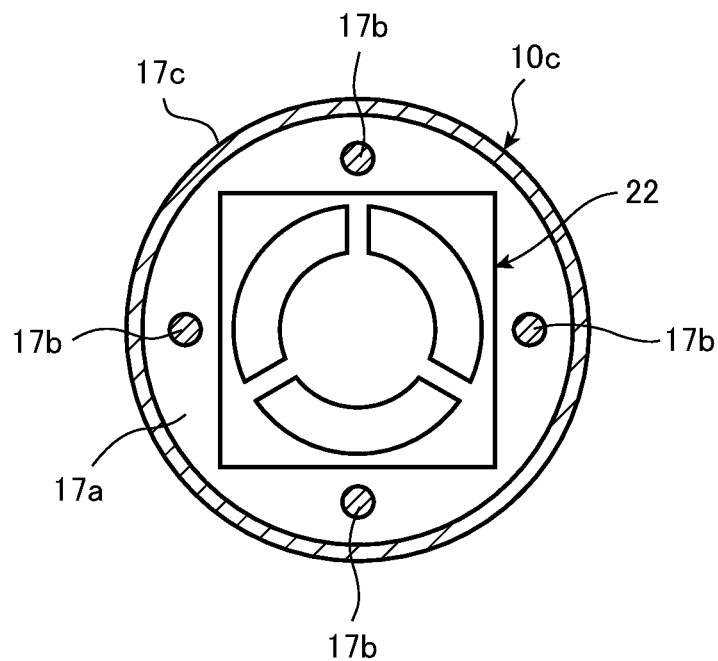
FIG. 4 is a cross-sectional view taken along the line B-B' of FIG. 3.

As shown in FIGS. 3 and 4, the connecting column 17b is configured from a column member of small diameter, and is provided projecting from a lower surface of the connecting main body portion 17a toward an upper surface of the downstream side housing 10b, such that its upper end is connected to the lower surface of the connecting main body portion 17a and its lower end is connected to the upper surface of the downstream side housing 10b. As shown in FIG. 4, four of these connecting columns 17b are provided at certain intervals in a circumferential direction, and the connecting columns 17b are configured so as not to hinder a flow of air.

The outflow direction regulating wall portion 17c is formed in a thin-walled cylindrical shape provided projecting from an entire circumferential edge region of the lower end of the connecting main body portion 17a toward the downstream side (lower end side of the housing 10). The outflow direction regulating wall portion 17c has a length in an axial direction reaching from the lower end of the connecting main body portion 17a to a position overlapping the upper end and close to the upper end of the downstream side housing 10b, and has an internal diameter larger than the external diameter of the downstream side housing 10b. That is, the outflow direction regulating wall portion 17c is an annular wall provided projecting from an entire circumferential edge region of the lower end of the connecting main body 17a toward the downstream side, so as to surround an outer surface of the upper end and close to the upper end of the downstream side housing 10b by its lower end and close to its lower end, and such that a gap (outflow port 16) is formed between an inner surface of the lower end and close to the lower end of the outflow direction regulating wall portion 17c and the outer surface of the upper end and close to the upper end of the downstream side housing 10b.

This outflow direction regulating wall portion 17c, along with an inner surface of the connecting main body portion 17a, is configured to form a flow path 12a communicating with the housing space 12 of the upstream side housing 10a. Moreover, the outflow direction regulating wall portion 17c is configured so as to demarcate the outflow port 16 at which air in the housing space 12 flows out via the flow path 12a, between the outflow direction regulating wall portion 17c and the outer surface of the upper end and close to the upper end of the downstream side housing 10b. As a result of the outflow direction regulating wall portion 17c being configured in this way, the outflow port 16 opens toward the downstream side over an entire region in the circumferential direction of the housing 10, such that air that has flowed out from the outflow port 16 via the housing space 12 and the flow path 12a flows along the outer surface of the downstream side housing 10b on a more downstream side than the outflow port 16.

As shown in FIGS. 1 and 3, the downstream side housing 10b is formed in a cylindrical shape having its upper end and lower end blocked, and has an external diameter smaller than the internal diameter of the outflow direction regulating wall portion 17c. The downstream side housing 10b has a length in its longitudinal direction sufficient to enable air that has flowed out from the outflow port 16 to flow along the outer surface of at least the upper end and close to the upper end of the downstream side housing 10b, when the downstream side housing 10b is connected to the connecting portion 10c. That is, the downstream side housing 10b has a length in its longitudinal direction enabling the outflow port 16 to be separated from the lower end of the housing 10 so as to prevent the outflow port 16 being blocked, even when, for example, the collecting apparatus 1 is housed in a confined space such as a breast pocket of an operator. The downstream side housing 10b is configured capable of housing in its internal space a control unit 24 and power supply unit 26 of the gas flow generator 20.

As shown in FIGS. 1 and 3, the gas flow generator 20 comprises: a fan 22 provided in the flow path 12a of the connecting portion 10c; the control unit 24 that controls drive of the fan 22; and the power supply unit 26 that supplies electric power for driving the fan 22. This fan 22 is configured such that drive thereof, along with causing air to flow into the housing space 12 from the inflow port 14, causes that air to flow at a constant speed toward the outflow port 16 and generates a gas flow of a certain speed within the housing space 12. Now, the fan 22 may be capable of generating a gas flow of a wind speed of under 0.5 m/sec, and a comparatively small-sized one may be employed. The control unit 24 is configured capable of executing ON/OFF operation of the fan 22. The power supply unit 26 may employ the likes of a dry cell, for example, and one of low electric power and small size may be employed. The control unit 24 and the power supply unit 26 are housed in the internal space of the downstream side housing 10b. These fan 22, control unit 24, and power supply unit 26 may employ well-known ones, moreover there is no need for them to have fine flow speed control, provided they are configured to generate a gas flow of a certain speed.

As shown in FIG. 1, the holding portion 30 is a rod-like member having its upper end configured capable of being connected to an upper surface of the lid member 11b of the upstream side housing 10a and its lower end configured capable of holding the collecting member 2. The holding portion 30 has a length in its longitudinal direction such that when its upper end is connected to the lid member 11b and the collecting member 2 is held at its lower end, the collecting member 2 fits inside the housing space 12 of the upstream side housing 10a. The upper end of the holding portion 30 has formed therein along an axial direction a screw hole into which a screw 18 can be helically inserted, and is configured so as to be attached to the lid member 11b, so as to be coaxial with the central axis of the upstream side housing 10a, by fastening power of the screw 18. Formed on a circumferential surface of the upper end and close to the upper end of the holding portion 30 is a screw (not illustrated) for attaching a helical air flow generator 15.

As shown in FIGS. 1 and 2, the turbulence generator 13 is configured from: the inflow port 14 formed in a circumferential surface of the lid member 10b; and the helical air flow generator 15 which is provided at a position aligned with the inflow port 14 on the inside of the upstream side housing 10a, and is capable of changing a flow direction of air that has flowed in from the inflow port 14. As shown in FIG. 1, the helical air flow generator 15 is formed in a truncated cone shape tapering toward the downstream side of the housing 10, and has formed from its upper surface to its bottom surface a screw hole (not illustrated) capable of engaging with the screw (not illustrated) formed in the circumferential surface of the upper end close to the upper end of the holding portion 30. This helical air flow generator 15 is attached on the circumferential surface of the upper end close to the upper end of the holding portion 30, such that its conical surface (that is, a curved surface tapering toward the downstream side of the housing 10 and curving in the circumferential direction) faces the inflow port 14.

As a result of the turbulence generator 13 according to the first embodiment, each of the inflow ports 14 is formed having its position misaligned in the circumferential direction so as not to be orthogonal to the central axis X4 of the lid member 11b, and the helical air flow generator 15 is provided at a position aligned with the inflow port 14, whereby air that has flowed in from the inflow port 14 can be caused to flow along the conical surface of the helical air flow generator 15 and a helical air flow can be generated in the housing space 12 of the upstream side housing 10a, hence a gas flow flowing through the housing space 12 can be rendered in a turbulent state.

Next, a method of collecting a substance-to-be-collected in the atmosphere using the collecting apparatus 1 according to the first embodiment and a method of calculating concentration of the substance-to-be-collected in the atmosphere from a collection amount of the substance-to-be-collected collected by this method of collecting, will be described.

In order to collect a substance-to-be-collected in the atmosphere using the collecting apparatus 1 according to the first embodiment, first, the lid member 11b is removed from the housing main body 11a, and then the collecting member 2 is taken out from an airtight bag, and an end of the collecting member 2 is held in the holding portion 30. Next, the lid member 11b is fitted to the housing main body 11a, such that the collecting member 2 is positioned within the housing space 12 of the upstream side housing 10a. Then, an operating switch (not illustrated) of the gas flow generator 20 is operated to drive the fan 22 and generate a gas flow of constant speed in the housing space 12. At this time, the gas flow in the housing space 12 attains a turbulent state, due to the turbulence generator 13. Then, a collecting surface of the collecting member 2 is exposed to the gas flow containing the substance-to-be-collected, and the substance-to-be-collected is collected in the collecting member 2 by the likes of a movement diffusion phenomenon or absorption. After a certain collection time has passed, drive of the fan 22 is stopped, and the lid member 11b is removed from the housing main body 11a and the collecting member 2 is returned to the airtight bag. Then, the collecting member 2 is conveyed to a measuring room, and a collection amount M of the substance-to-be-collected collected in the collecting member 2 is measured by a variety of well-known methods, in the measuring room.

In order to calculate concentration of the substance-to-be-collected in the atmosphere using the collecting apparatus 1 according to the first embodiment, first, a unit collecting speed J with respect to the substance-to-be-collected of the collecting member 2 used is calculated from Fick's first law of diffusion equation ($J=D \times C/L$). Now, the collecting apparatus 1 according to the first embodiment forcibly generates at constant speed the gas flow to which the collecting member 2 is exposed, thereby eliminating an influence of wind speed in a measurement environment, and a value of a diffusion length L, that is, a length from an inlet port of the collecting member 2 to a collecting surface, can be set constant, hence the unit collecting speed J can be calculated accurately reflecting Fick's first law of diffusion equation. Now, in Fick's first law of diffusion equation, D indicates a molecular diffusion coefficient of the substance-to-be-collected, C indicates a concentration in a periphery, and C/L means a concentration gradient.

Next, a total collecting speed, that is, a sampling rate SR is calculated from equation ($SR=A \times D \times C/L$), based on a value of the unit collecting speed J obtained from Fick's first law of diffusion equation ($J=D \times C/L$) and a collecting area A of the collecting member 2. This sampling rate SR is a characteristic collecting speed of a collecting substance with respect to a specific substance-to-be-collected. Now, a dimensional unit of the sampling rate SR is [μg/(ppm×min)].

Next, a concentration C' of the substance-to-be-collected in the atmosphere is calculated from equation ($C'=M/(SR \times t)$), based on a value of the sampling rate SR obtained from equation ($SR=A \times D \times C/L$), a value of the collection amount M of the substance-to-be-collected actually collected by the collecting member 2, and a value of a collection time t.

Such a concentration measuring method makes it possible to theoretically estimate the sampling rate SR of substantially all of the diffusing substance-to-be-collected by equation ($SR=A \times D \times C/L$), accurately reflecting Fick's first law of diffusion equation ($J=D \times C/L$). Moreover, by estimate of the sampling rate SR being made possible, concentration of the substance-to-be-collected in the atmosphere can be accurately calculated by equation ($C'=M/(SR \times t)$), hence a highly accurate concentration measurement can be made possible.

As mentioned above, the collecting apparatus 1 according to the first embodiment comprises: the housing 10 which is long and includes the housing space 12 capable of housing the collecting member 2, the housing 10 having formed therein the inflow port 14 and the outflow port 16, the inflow port 14 enabling air in the atmosphere to flow in to the housing space 12, and the outflow port 16 enabling air in the housing space 12 to flow out; the gas flow generator 20 that generates a gas flow within the housing space 12, so as to allow air in the housing space 12 to flow in from the inflow port 14 and cause that air to flow toward the outflow port 16; and the holding portion 30 that holds the collecting member 2 in a position that the gas flow flows, the inflow port 14 being formed on a more upstream side than the collecting member 2 held by the holding portion 30, and the outflow port 16 being formed on a more downstream side than the collecting member 2 held by the holding portion 30, and the outflow port 16 opening toward the downstream side such that air that has flowed out from the outflow port 16 flows along the housing outer surface on a more downstream side than the outflow port 16. Therefore, the collecting apparatus 1 according to the first embodiment results in the outflow port 16 opening toward the downstream side such that air that has flowed out from the outflow port 16 flows along the housing outer surface on a more downstream side than the outflow port 16, whereby even when, for example, the device is carried housed in a confined space such as a breast pocket of an operator, such that the inflow port 14 is positioned outside the breast pocket and the outflow port 16 is positioned inside the breast pocket, the outflow port 16 is never blocked. Therefore, the collecting apparatus 1 according to the first embodiment makes it possible for collection of the substance-to-be-collected to be performed without any problem, even when, for example, collection of the substance-to-be-collected is performed while the device is carried housed in the likes of a breast pocket of an operator.

Moreover, as mentioned above, in the collecting apparatus 1 according to the first embodiment, the housing 10 comprises: the upstream side housing 10a that includes the housing space 12; the downstream side housing 10b connected to a downstream side of the upstream side housing 10a; and the connecting portion 10c that connects the upstream side housing 10a and the downstream side housing 10b, and the connecting portion 10c includes the cylindrical outflow direction regulating wall portion 17c provided projecting toward the downstream side housing 10b so as to surround the outer surface of the upper end and close to the upper end of the downstream side housing 10b, and is configured such that the gap formed between the inner surface of the outflow direction regulating wall portion 17c and the outer surface of the upper end and close to the upper end of the downstream side housing 10b functions as the outflow port 16. Such a collecting apparatus 1 according to the first embodiment results in the outflow port 16 being formed over an entire region in the circumferential direction of the housing 10, hence even if part of the outflow port 16 is blocked when, for example, the device is housed in a confined space such as a breast pocket of an operator, air discharge can be performed and an air flow can be generated without any problem.

Furthermore, as mentioned above, in the collecting apparatus 1 according to the first embodiment, the gas flow generator 20 comprises: the fan 22 that generates the gas flow; the control unit 24 that controls drive of the fan 22; and the power supply unit 26 that supplies electric power for driving the fan 22, and the control unit 24 and power supply unit 26 are housed in the downstream side housing 10b. Such a collecting apparatus 1 according to the first embodiment results in the downstream side housing 10b not only functioning as a spacer for distancing the outflow port 16 from the lower end of the housing 10 and preventing blockage of the outflow port 16, but also functioning as a housing member for housing the control unit 24 and power supply unit 26, hence the collecting apparatus 1 can be more miniaturized compared to when the control unit 24 and power supply unit 26 are housed in a housing member other than the downstream side housing 10b.

Still further, as mentioned above, in the collecting apparatus 1 according to the first embodiment, the housing 10 is formed in a cylindrical shape having its end on an upstream side blocked, and a plurality of the inflow ports 14 are formed at certain intervals in the circumferential direction of the housing 10, in a region of not more than three quarters of an entire region in the circumferential direction of the housing 10. Such a collecting apparatus 1 according to the first embodiment makes it possible for the collecting apparatus 1 to be carried housed in, for example, a breast pocket of an operator, in a state that a region where the inflow port 14 is not formed (a region of one quarter of the entire region in the circumferential direction of the housing 10) is directed to an operator side, and a region where the inflow port 14 is formed (a region of three quarters of the entire region in the circumferential direction of the housing 10) is directed in a direction of increasing distance from the operator (to an atmosphere side). That is, in the case that the inflow port 14 is formed in the entire region in the circumferential direction of the housing 10, there is a risk that when, for example, the collecting apparatus 1 is carried housed in a breast pocket of an operator, part of the inflow port 14 is blocked by being in close contact with the operator, and that the gas flow cannot be stably generated. In contrast, in the collecting apparatus 1 according to the first embodiment, the region directed to the operator side when, for example, the collecting apparatus 1 is housed in the breast pocket of an operator (region of one quarter of the entire region in the circumferential direction of the housing 10) does not have the inflow port 14 formed therein, hence an unanticipated partial blockage of the inflow port 14 can be prevented.

Figure 8:
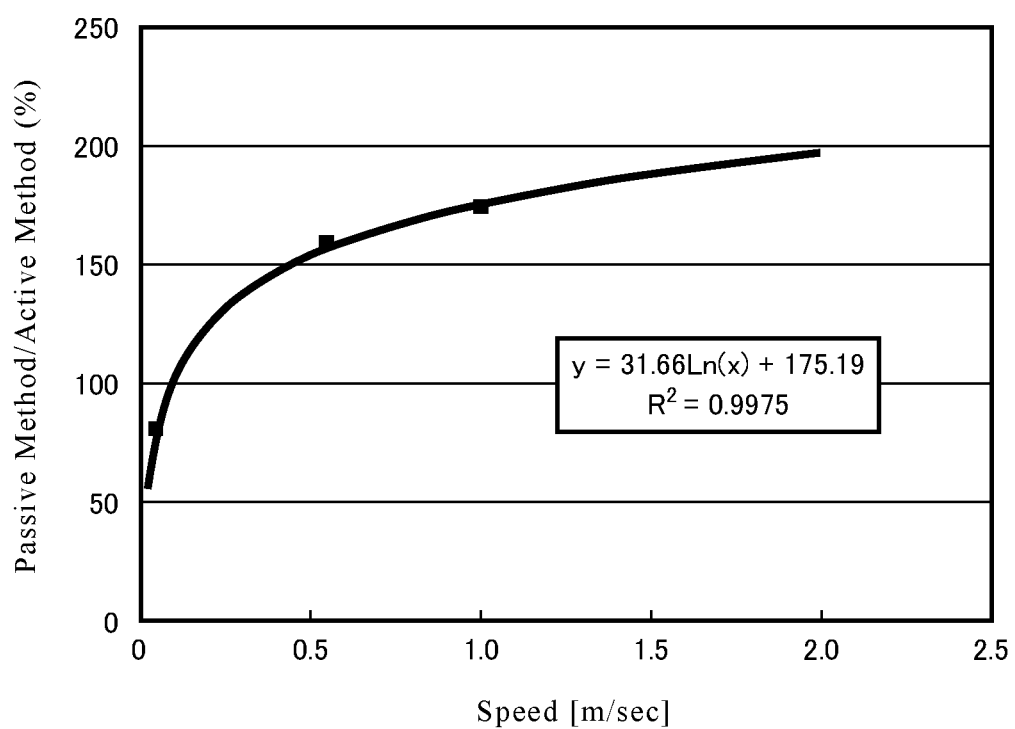
FIG. 8 is a graph showing a relationship between collection amount of a passive sampler and wind speed.

Moreover, as mentioned above, the collecting apparatus 1 according to the first embodiment further comprises the turbulence generator 13 which is provided more to an upstream side than the collecting member 2 held by the holding portion 30 and is configured to render the gas flow in a turbulent state. Such a collecting apparatus 1 according to the first embodiment makes it possible for stable collection of the substance-to-be-collected to be enabled, even when wind speed of the gas flow flowing through the housing space 12 of the housing 10 is a low wind speed of under 0.5 m/sec. That is, in a conventional collecting apparatus 300 shown in FIG. 9, from results of the graph shown in FIG. 8, if wind speed of a gas flow flowing within a housing 310 is not set to 0.5 m/sec or more, particularly to 1.0 m/sec or more, then stable collection cannot be performed, and strict control is required such that wind speed does not become less than 0.5 m/sec. Accordingly, the inventors of the present invention, as a result of continued diligent research into how stable collection of the substance-to-be-collected can be enabled even when, for example, wind speed is a low wind speed of under 0.5 m/sec, discovered that by rendering the gas flow flowing in the housing in a turbulent state, stable collection of the substance-to-be-collected can be performed even when, for example, wind speed is a low wind speed of under 0.5 m/sec. Therefore, as a result of the collecting apparatus 1 according to the first embodiment comprising the turbulence generator 13, it is unnecessary for the wind speed of the gas flow flowing in the housing space 12 of the housing 10 to be set to 0.5 m/sec or more, hence there is no need for a large-sized fan or battery to be employed, moreover rotational speed of the fan can be suppressed, whereby a low-noise collecting apparatus capable of miniaturization and weight reduction can be adopted.

Furthermore, the collecting apparatus 1 according to the first embodiment is a device of a simple structure in which the gas flow is generated in the housing space 12 of the housing 10 by a dry cell-driven fan 22, hence can be used even in a place where securing of a power supply is difficult, moreover enables the likes of a diffusion survey from a substance-to-be-collected generation source such as an expressway or production plant, for example, to be implemented, at low cost, by a survey method where a large number of measurement places are set.

The collecting apparatus according to the present invention is not limited to the above-mentioned embodiment, and a variety of modifications may be performed within a range not departing from a technical idea of the present invention.

For example, in FIG. 1, a tube-type passive sampler was illustrated as the collecting member 2, but the collecting member is not limited to this, and a variety of collecting members may be employed, moreover a shape of the housing may undergo a variety of modifications according to a type and shape of the collecting member used. Furthermore, the collecting apparatus 1 according to the first embodiment may be a collecting apparatus for environmental tobacco smoke (ETS) personal exposure amount measurement that uses as the collecting member a polyurethane foam (PUF) capable of absorbing nicotine, for example.

In the collecting apparatus 1 according to the first embodiment, the housing 10 was described as comprising the upstream side housing 10a, the downstream side housing 10b, and the connecting portion 10c, but is not limited to this. In the collecting apparatus according to the present invention, a variety of housings may be employed, provided that the housing includes the housing space capable of housing the collecting member and that the housing has formed therein the inflow port enabling air in the atmosphere to flow in to the housing space and the outflow port enabling air in the housing space to flow out.

In the collecting apparatus 1 according to the first embodiment, it was assumed that three of the inflow ports 14 are formed, and that these inflow ports 14 are formed having their positions misaligned in the circumferential direction such that their central axes X1, X2, and X3 are not orthogonal to the central axis X4 of the housing main body 11a, but the inflow port 14 is not limited to this, and it is only required that at least one inflow port 14 is formed, moreover the inflow port 14 need not be formed having its position misaligned in the circumferential direction. That is, in the collecting apparatus according to the present invention, the inflow port may comprise any configuration, provided it is a configuration in which the inflow port is formed on a more upstream side than the collecting member held by the holding portion and enables air in the atmosphere to flow in to the housing space of the housing.

In the collecting apparatus 1 according to the first embodiment, the outflow port 16 was described as being demarcated by the inner surface of the outflow direction regulating wall portion 17c and the outer surface of the upper end and close to the upper end of the downstream side housing 10b, but is not limited to this. In the collecting apparatus according to the present invention, the outflow port may comprise any configuration, provided it is formed on a more downstream side than the collecting member held by the holding portion and opens toward the downstream side such that air that has flowed out from said outflow port flows along the housing outer surface on a more downstream side than said outflow port.

In the collecting apparatus 1 according to the first embodiment, the gas flow generator 20 was described as comprising the fan 22, the control unit 24, and the power supply unit 26, but is not limited to this, and may comprise any configuration, provided it generates a gas flow in the housing space so as to cause air to flow into the housing space from the inflow port of the housing and cause that air to flow toward the outflow port.

In the collecting apparatus 1 according to the first embodiment, the holding portion 30 was described as a rod-like member having its upper end configured capable of being connected to the upper surface of the lid member 11b of the upstream side housing 10a and its lower end configured capable of holding the collecting member 2, but is not limited to this, and may comprise any configuration, provided it holds the collecting member in a position that the gas flow flows.

In the collecting apparatus 1 according to the first embodiment, the turbulence generator 13 was assumed to be configured from the inflow port 14 and the helical air flow generator 15, but is not limited to this, and the turbulence generator may adopt a variety of configurations, provided it is a configuration in which the turbulence generator renders the gas flow flowing in the housing space 12 of the housing 10 in a turbulent state. Moreover, the collecting apparatus according to the present invention may be configured not comprising the turbulence generator, as in the conventional collecting apparatus 300 shown in FIG. 9, for example.

Figure 5:
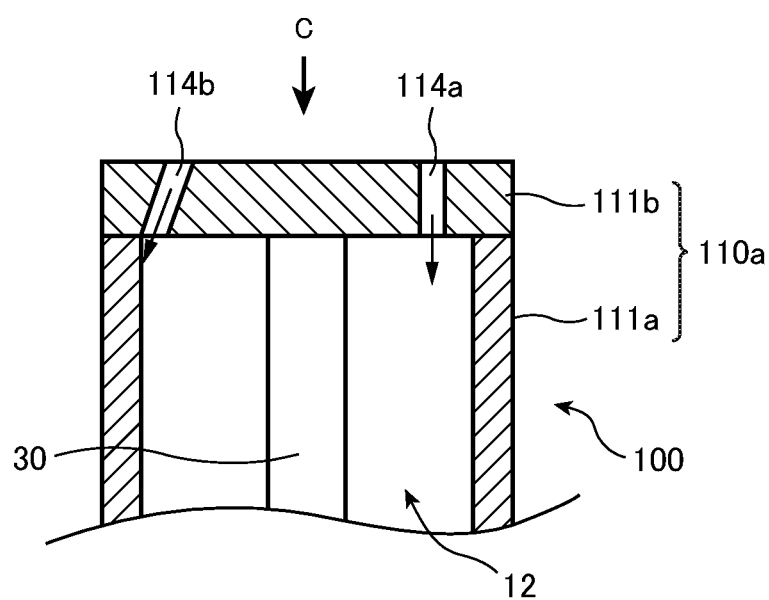
FIG. 5 is a partial cross-sectional view showing a schematic configuration of a collecting apparatus according to a second embodiment of the present invention.
Figure 6:
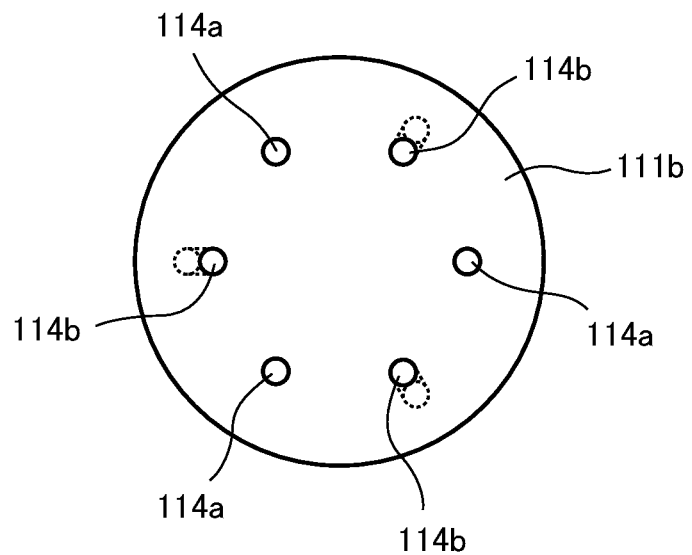
FIG. 6 is a lateral view showing a state where the collecting apparatus according to the second embodiment is seen from the direction C shown in FIG. 6.
Figure 7:
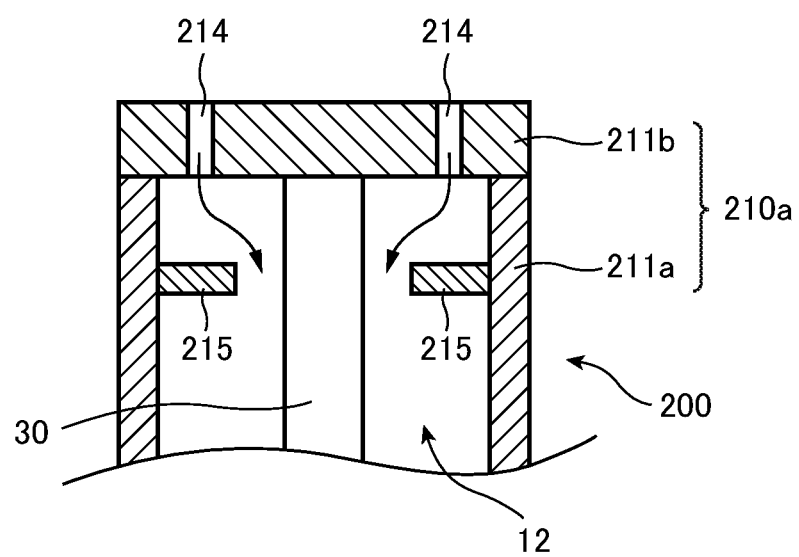
FIG. 7 is a partial cross-sectional view showing a schematic configuration of a collecting apparatus according to a third embodiment of the present invention.

FIGS. 5 and 6 show a second example of a turbulence generator (collecting apparatus 100 according to a second embodiment), and FIG. 7 shows a third example of a turbulence generator (collecting apparatus 200 according to a third embodiment). Note that in the collecting apparatuses 100 and 200 of the second and third embodiments, configurations of the housing main body and lid member of the upstream side housing, the inflow port, and other than the turbulence generator are similar to configurations of the collecting apparatus 1 according to the first embodiment, hence descriptions thereof will be omitted. Moreover, collecting methods and concentration measuring methods performed using the collecting apparatuses 100 and 200 according to the second and third embodiments are similar to the collecting method and concentration measuring method performed using the collecting apparatus 1 according to the first embodiment, hence descriptions thereof will be omitted.

As shown in FIG. 5, an upstream side housing 110a of the collecting apparatus 100 according to the second embodiment comprises: a housing main body 111a formed in a cylindrical shape; and a lid member 111b which is disc-shaped and blocks an opening on an upstream side of the housing main body 111a. As shown in FIGS. 5 and 6, formed in the lid member 111b, from its upstream side surface (upper side surface in FIG. 5) to its downstream side surface (lower side surface in FIG. 5), are three perpendicular inflow ports 114a penetrating along an axial direction of the housing main body 111a and three inclined inflow ports 114b penetrating inclined in a direction intersecting the axial direction of the housing main body 111a. These perpendicular inflow ports 114a and inclined inflow ports 114b have a diameter that enables air in the atmosphere to flow in to the housing space 12 and are configured so as not to hinder operation and function of the gas flow generator 20. As shown in FIG. 6, these perpendicular inflow ports 114a and inclined inflow ports 114b are formed alternately, arranged at equal intervals, on a circumference of an identical circle centered around a center of the lid member 111b.

In the collecting apparatus 100 according to the second embodiment, the inclined inflow port 114b penetrates in a direction intersecting the axial direction of the housing main body 111a, hence a flow of air flowing into the housing 10 via said inclined inflow port 114b can be caused to differ from the axial direction of the housing main body 111a, whereby a flow of an air flow flowing in the housing 10 can be disturbed and rendered in a turbulent state. Thus, in the collecting apparatus 100 according to the second embodiment, the inclined inflow port 114b functions as the turbulence generator. Note that in the collecting apparatus 100 according to the second embodiment, it was assumed that there are respectively three each of the perpendicular inflow ports 114a and inclined inflow ports 114b formed, and that these perpendicular inflow ports 114a and inclined inflow ports 114b are formed alternately, arranged at equal intervals, on the circumference of an identical circle centered around the center of the lid member 111b, but the perpendicular inflow port 114a and inclined inflow port 114b are not limited to this, and all that is required is a configuration enabling the gas flow flowing in the housing 10 to be rendered in a turbulent state, and that at least one inclined inflow port 114b is formed.

As shown in FIG. 7, the collecting apparatus 200 according to the third embodiment has perpendicular inflow ports instead of configuring three of the inclined inflow ports of the collecting apparatus 100 according to the second embodiment, and is provided with a plate-like changing member (turbulence generator) 215 capable of changing a flow direction of air that has flowed in from the perpendicular inflow port. That is, contrary to the lid member 111b of the collecting apparatus 100 according to the second embodiment, a lid member 211b of the collecting apparatus 200 according to the third embodiment has only a perpendicular inflow port 214 formed therein.

The turbulence generator 215 is configured from a plurality of plate members and is disposed standing perpendicularly on an inner surface of a housing main body 211a, such that one surface of the turbulence generator 215 faces the perpendicular inflow port 214. Such a turbulence generator 215 makes it possible for a flow of air that has flowed in from the perpendicular inflow port 214 to be disturbed and a gas flow flowing in the housing space 12 of an upstream side housing 210a to be rendered in a turbulent state. Note that in the collecting apparatus 200 according to the third embodiment, the turbulence generator 215 was assumed to be configured from a plurality of plate members, but is not limited to this, and may be of any kind, provided it is capable of changing the flow direction of air that has flowed in from the inflow port of the housing, that is, provided it can disturb the flow of air that has flowed in from the inflow port and render the gas flow in a turbulent state. For example, the turbulence generator 215 may adopt a variety of configurations such as a filter paper, a non-woven fabric, a metal net, and so on, that are sufficiently coarse to be able to hinder the flow of air. Moreover, in the collecting apparatus 200 according to the third embodiment, the inflow port was assumed to be configured from a plurality of perpendicular inflow ports, but is not limited to this, and may be of any configuration, provided it is a configuration enabling air in the atmosphere to flow in to the housing space 12 of the upstream side housing 210a, for example, may be configured from one perpendicular inflow port or one or a plurality of inclined inflow ports, or may be configured from one or more perpendicular inflow ports and one or more inclined inflow ports.

DESCRIPTION OF REFERENCE NUMERALS 1, 100, 200 collecting apparatus
2 collecting member
10 housing 10a upstream side housing
10b downstream side housing
10c connecting portion
12 housing space
13 turbulence generator
14 inflow port
16 outflow port
17c outflow direction regulating wall portion
20 gas flow generator
22 fan
24 control unit
26 power supply unit
30 holding portion
114b inclined inflow port (turbulence generator)
215 turbulence generator

The invention claimed is:

1. A collecting apparatus that employs a collecting member to collect a substance-to-be-collected in the atmosphere, the collecting apparatus comprising:
 a housing which is long and includes a housing space capable of housing the collecting member, the housing having formed therein an inflow port and an outflow port, the inflow port enabling air in the atmosphere to flow into said housing space, and the outflow port enabling air in the housing space to flow out;
 a gas flow generator that generates a gas flow within the housing space, so as to allow air in the housing space to flow in from the inflow port and cause that air to flow toward the outflow port; and
 a holding portion attached to the housing that holds the collecting member in a position that the gas flow flows,
 the housing comprising: an upstream side housing that includes the housing space; a downstream side housing connected to a downstream side of the upstream side housing; and a connecting portion that connects the upstream side housing and the downstream side housing,
 the connecting portion including an outflow direction regulating wall portion of cylindrical shape having an internal diameter larger than an external diameter of the downstream side housing, wherein the outflow direction regulating wall portion is provided projecting toward the downstream side housing so as to surround an outer surface of an upper end and close to the upper end of the downstream side housing,
 the inflow port being formed on a more upstream side than the collecting member held by the holding portion, and
 the outflow port being a gap formed between an inner surface of the outflow direction regulating wall portion and an outer surface of the upper end and close to the upper end of the downstream side housing, and, on a more downstream side than the collecting member held by the holding portion, the outflow port opening toward the downstream side such that air that has flowed out from said outflow port flows along an outer surface of the housing that is downstream of said outflow port.

2. The collecting apparatus according to claim 1, wherein the gas flow generator comprises: a fan that generates the gas flow; a control unit that controls drive of the fan; and a power supply unit that supplies electric power for driving the fan, and
 the control unit and the power supply unit are housed in the downstream side housing.

3. The collecting apparatus according to claim 1, wherein the housing is formed in a cylindrical shape having its end side on an upstream side blocked, and
 a plurality of the inflow ports are formed at certain intervals in a circumferential direction of the housing, in a region of not more than three quarters of an entire region in the circumferential direction of the housing.

4. The collecting apparatus according to claim 1, further comprising: a turbulence generator provided on a more upstream side than the collecting member held by the holding portion, the turbulence generator being configured to render the gas flow in a turbulent state.

* * * * *